United States Patent [19]
Pelletier

[11] Patent Number: 5,862,273
[45] Date of Patent: Jan. 19, 1999

[54] FIBER OPTIC PROBE WITH INTEGRAL OPTICAL FILTERING

[75] Inventor: Michael J. Pelletier, Saline, Mich.

[73] Assignee: Kaiser Optical Systems, Inc., Ann Arbor, Mich.

[21] Appl. No.: 803,012

[22] Filed: Feb. 21, 1997

Related U.S. Application Data

[60] Provisional application No. 60/012,137 Feb. 23, 1996.

[51] Int. Cl.⁶ .................................................... G02B 6/00
[52] U.S. Cl. ............................................................. 385/12
[58] Field of Search ................................... 356/318, 317, 356/402, 301, 442; 385/12, 13, 115–121; 250/227.15, 458.1, 459.1

[56] References Cited

U.S. PATENT DOCUMENTS

| | | | |
|---|---|---|---|
| 4,573,761 | 3/1986 | McLachlan et al. | 350/96.24 |
| 4,807,950 | 2/1989 | Glenn et al. | 350/3.61 |
| 5,216,483 | 6/1993 | Berthold et al. | 356/318 |
| 5,283,686 | 2/1994 | Huber | 359/337 |
| 5,367,588 | 11/1994 | Hill et al. | 385/37 |
| 5,615,008 | 3/1997 | Stachelek | 356/301 |
| 5,652,810 | 7/1997 | Tipton et al. | 385/12 |
| 5,705,821 | 1/1998 | Barton et al. | 250/458.1 |
| 5,710,626 | 1/1998 | O'Rourke et al. | 356/301 |

OTHER PUBLICATIONS

T. Strasser, T. Erdogan, A.White, V. Mizrahi, P. Lemaire, "Ultraviolet laser fabrication of strong, nearly polarization–independent Bragg reflectors in germanium–doped silica waveguides on silica substrates", *App. Phys. Lett.* 65(26), 26 Dec. 1994.

P. Niay, P. Bernage, S. Legoubin, M. Douay, W. Xie, J. Bayon, T. Georges, M. Monerie, B. Poumellec, "Behaviour of spectral transmissions of Bragg gratings written in germania–doped fibres: writing and erasing experiments using pulsed or cw uv exposure", *Optics Communications* 113 (1994) pp. 176–192.

W. Morey, G. Ball, G. Meltz, "Photoinduced Bragg Gratings in Optical Fibers", *Optics & Photonics News,* Feb. 1994, pp. 8–14.

L. Zhang, K. Sugden, J. Williams, I. Bennion, "Postfabrication exposure of gap–type bandpass filters in broadly chirped fiber gratings", *Optics Letters,* Sep. 15, 1995, vol. 20, No. 18, pp. 1927–1929.

P. Lemaire, R. Atkins, V. Mizrahi, W. Reed, "High Pressure $H_2$ Loading as a Technique for Achieving Ultrahigh UV Photosensitivity and Thermal Sensitivity in $GeO_2$ Doped Optical Fibers", *Electronic Letters,* 24 Jun. 1993, vol. 29, No. 13, pp. 1191–1193.

G. Meltz, W. Morey, W. Glenn, "Formation of Bragg gratings in optical fibres by a transverse holographic method", *Optics Letters,* Aug. 1, 1989, vol. 14, No. 15, pp. 823–825.

(List continued on next page.)

*Primary Examiner*—Akm E. Ullah
*Attorney, Agent, or Firm*—Gifford, Krass, Groh, Sprinkle, Patmore, Anderson & Citkowski

[57] ABSTRACT

Laser band-pass filter and/or band-reject filters are located at the end of an optical measurement probe by placing an appropriate Bragg grating proximate to the tip, and within, one or both of the optical fibers that make up the probehead. Thus, where an optical fiber is used to carry excitation energy of a nominal wavelength to a sample, the distal tip of this fiber will have included therein an optical filter to selectively pass energy of the nominal wavelength. Similarly, where an optical fiber is employed to carry stimulated emission from the sample to an analytical instrument such as a spectrometer, this fiber will have included within it at its distal tip an optical filter to selectively reject energy associated with the nominal wavelength. A disclosed system-level optical measurement probe would include a laser, a spectrometer, a first optical fiber to carry energy from the laser to a sample, including a Bragg grating laser bandpass filter at its tip, and a second optical fiber to carry energy collected from the sample to the spectrometer, including a Bragg grating laser band-reject filter at its tip.

25 Claims, 2 Drawing Sheets

OTHER PUBLICATIONS

K. Tanaka, N. Toyosawa, H. Hisakuni, "Photoinduced Bragg gratings in $As_2S_3$ optical fibers", *Optics Letters,* vol. 20, No. 19, Oct. 1, 1995, pp. 1976–1978.

L. Dong, J. Cruz, J. Tucknott, L. Reekie, D. Payne, "Strong photosensitive gratings in tin–doped phosphosilicate optical fibers", *Optics Letters,* vol. 20, No. 19, Oct. 1, 1995, pp. 1982–1984.

L. Dong, J. Archambault, E. Taylor, M. Roe, L. Reekie, P. Russell, "Photosensitivity in tantalum–doped silica optical fibers", *J. Opt. Soc. Am. B,* vol. 12, No. 9, Sep. 1995, pp. 1747–1750.

L. Dong, J. Archambault, L. Reekie, P. Russell, D. Payne, "Photoinduced absorption change in germanosilicate preforms: evidence for the color–center model of photosensitivity", *Applied Optics,* vol. 34, No. 18, 20 Jun. 1995, pp. 3436–3440.

M. Miller, R. Linton, S. Bush, J. Jorgenson, "Correlation of Retention Behavior with Quantitative Surface Analysis of Octadecyl Bonded Chromatographic Supports", *Anal. Chem.,* 1984, 56, pp. 2204–2210.

C. Brooks, G. Vossler, K. Winick, "Integrated–optic dispersion compensator that uses chirped gratings", *Optics Letters,* vol. 20, No. 4, Feb. 15, 1995, pp. 368–370.

H. Hisakuni, K. Tanaka, "Optical Microfabrication of Chalcogenide Glasses", *Science,* vol. 270, 10 Nov. 1995, pp. 974–975.

R. Needham, M. Delaney, "Cadmium Telluride γ–Ray Liquid Chromatography Detector for Radio–pharmaceuticals", *Anal. Chem.,* 1983, 55, p. 148.

M. Leugers, R. McLachlan, "Remote analysis fiber optic Raman spectroscopy", *SPIE,* vol. 990, 1988, pp. 88–95.

{Author Unknown}, "Fiber Optic Probe for Remote Raman Spectrometry", *Anal. Chem.,* 1983, 55, pp. 146–147.

S. Schwab, R. McCreery, "Versatile, Efficient Raman Sampling with Fiber Optics", *Anal. Chem.,* 1984, 56, pp. 2199–2203.

FIBER OPTIC PROBE WITH INTEGRAL OPTICAL FILTERING

REFERENCE TO RELATED APPLICATION

This application claims priority of U.S. provisional application Ser. No. 60/012,137, filed Feb. 23, 1996, the entire contents of which are incorporated herein by reference.

FIELD OF THE INVENTION

This invention relates generally to the measurement of radiative optical effects and, in particular, to an optical fiber based probe having laser bandpass and/or band-reject filters integrated directly into the material of the fibers.

BACKGROUND OF THRU INVENTION

Fiber-optic probes make it possible to collect optical information such as Raman spectra without having to place the material being characterized inside a spectrometer housing. Such probes therefore simplify the interfacing of spectroscopic systems to chemical processes, and allow analytical instruments to be located remotely from hostile environments in need of spectroscopic monitoring.

The first remote fiber optic probes for Raman spectroscopy were reported by the McCreery group in the early 1980's. Their design used a single optical fiber to deliver laser light to the sample and a single optical fiber to collect light scattered by the sample. More specifically, divergent laser light from the laser delivery fiber was used to illuminate the sample, and light scattered from the sample within the acceptance cone of the collection fiber was transmitted back to the spectrograph. The efficiency of exciting and collecting Raman photons from any individual point in the sample was poor, but the integrated Raman intensity over the unusually large analysis volume compared favorably with the more traditional imaged illumination and collection.

McCreery's dual fiber Raman probe offered important benefits for remote and routine spectroscopy: 1) the sample could be distant from the Raman instrument, 2) no sample alignment was necessary once the probe was aligned to the spectrograph, 3) the probe could be less 1mm in diameter, making Raman measurements possible for samples with limited accessibility, 4) the probe could be placed directly in hostile samples (corrosive, hot, etc.) since only silica and the encapsulation material were exposed, and 5) multiple measurements could be made simultaneously by placing multiple collection fibers along the slit height of the spectrograph.

Several improvements to the McCreery Raman probe have more recently been reported. Instead of using just one collection fiber, multiple fibers have been used to increase the collection efficiency. For example, 6 fibers, each having the same diameter as the excitation fiber, may be grouped around the excitation fiber to form a single circular layer, as shown in U.S. Pat. No. 4,573,761. Eighteen fibers, each having the same diameter as the excitation fiber, may also be grouped around the excitation fiber as two circular layers, and so on, though successive layers tend to be less effective at collecting Raman photons than the first layer.

The performance of the McCreery type probe can also be modified for improved collection efficiency and/or working distance by changing the overlap between the emission cone of the excitation fiber and the collection cones of the collection fibers. The first realization of this idea, reported by Leugers et al, angled the collection fibers such that their optic axes intersected the optic axis of the illumination fiber. This increased the overlap of the excitation and collection cones close to the tip of the fiber probe, where the excitation and collection of Raman photons was most efficient. The same concept was later implemented in a different way by O'Rourke and Livingston, who ground the tip of the probe into a cone shape, as discussed in U.S. Pat. No. 5,402,508. This shape was equivalent to putting prisms (or more correctly, axicon sections) on the collection fibers so that their optic axes crossed the optic axis of the excitation fiber.

One further variation of the McCreery probe design is to use collection fibers having a different diameter than the excitation fiber. This additional variable is useful for changing the working distance of the probe and the fiber coupling to the spectrograph. It is unclear how this changes the collection efficiency, however.

A serious problem with all of the fiber optic Raman robes discussed so far is probe background. Laser light inside an optical fiber generates Raman and fluorescence emission from the fiber core itself. This emission can overwhelm the desired Raman signal from the sample, and is the reason why the intense excitation light must be carried by a fiber separate from the collection fiber(s). Nevertheless, such emissions generated in the excitation fiber can result in unwanted reflection from the sample into the collection cones of the collection fibers. Furthermore, laser light reflected from the sample into the collection cones of the collection fibers may generate unwanted emission while propagating through the collection fibers back to the spectrograph. Symmetry arguments predict that the optical fiber emission observed at the spectrograph will have equal contributions from the excitation fiber and the collection fibers if the length of the excitation fiber is the same as the length of the collection fibers.

When a McCreery-style probe is inserted into a transparent solution, or into a homogeneous, partially absorbing solution, reflection of laser light or fiber emission back to the collection fibers is negligible and the optical fiber emission is not observed. Rather, it is the Raman spectra of scattering samples which tends to suffer from probe background. The impact of this background can sometimes be reduced to acceptable levels by angling the probe with respect to the sample surface normal, by eliminating the spectral region containing the fiber emission from the analysis, or by spectral subtraction of the fiber emission.

For many Raman applications elimination of the optical fiber background is at least desirable, if not necessary. The O'Rourke group and others have inserted a thin-film dielectric interference filter into the excitation fiber to filter out some of the optical fiber background. A technique to carry this out is to place the filter inside an SMA-to-SMA connector and put the fibers in contact with the filter. Another way to accomplish this is to collimate the laser output from a fiber, send the collimated beam through the filter, and focus the transmitted light back onto the other fiber. Both approaches require precise alignment and attenuate the laser energy. More importantly, the laser energy must still travel through several centimeters to several meters of fiber between the filter and the probe tip, depending on geometry constraints of the specific application. Emission from this intermediate length of fiber optic cable remained a serious problem.

In-line filters can also be added to the collection fibers, but the same limitations apply. In addition, the use of separate filters on each collection fiber rapidly becomes impractical. The use of a single filter for the collection fiber bundle requires precise rotational alignment, in addition to precise translational alignment. One other approach, coupling the collection fiber bundle to a single large fiber prior to filtering, seriously reduces optical throughput because the larger fiber couples more poorly to the associated spectrograph(s).

A more effective approach for eliminating optical fiber background is described in U.S. Pat. No. 5,112,127, wherein an optical probehead located between the sample and the optical fibers is used to remove the fiber background from the excitation fiber and to remove scattered laser light before the Raman signal reaches the collection fiber. An improved probehead based on this concept was later described in commonly assigned U.S. Pat. No. 5,377,004, which is incorporated herein by reference.

An additional feature of these probeheads involves the use of imaged excitation and collection. A block diagram of such a system is illustrated FIG. 1, along with the spectral content of the optical energy present at various points along the illumination and collection paths. Energy from an excitation laser 102 is coupled into the illumination fiber 104, beginning as a relatively pure, single wavelength of light as illustrated by the graph 106, which plots intensity as a function of wave number. Upon traversing fiber 104, the laser energy induces Raman scattering within the fiber material, typically composed of silica, yielding a spectrum 108 at the output of the illumination fiber which contains spurious Raman lines in addition to the laser wavelength.

Unless these undesired lines are eliminated from the illumination path before reaching the sample, their Rayleigh scatter at the sample may be indistinguishable from the true, shifted Raman scatter due to the laser excitation of the sample. Therefore, a laser band pass device 110 is used to remove these unwanted wavelengths, thereby outputting, ideally, the single laser line shown in graph 112 to the illumination optic 114 and sample under characterization 120 along path 116. It is assumed for the purposes of this discussion that illumination optic 114 contains a sufficiently short optical path that it does not itself generate significant spurious scattering.

The light scattered by sample 120, depicted by line 122, is collected by collection optic 124. At the output of collection optic 124, as depicted in graph 126, the scattered radiation consists of the unshifted Rayleigh scatter at the laser wavelength and the shifted Raman scatter that characterizes the sample 120 under test. Since the Rayleigh scatter is several orders of magnitude stronger than the Raman scatter, if allowed to enter collection fiber 130, this strong Rayleigh scatter can excite spurious Raman scattering within collection fiber 130 similar to this situation within illumination fiber 104.

This Rayleigh scatter must therefore be rejected before being coupled to collection fiber 130. This may be accomplished with a Rayleigh rejection element 132, which generates the spectra depicted in graph 134, now devoid of the strong Rayleigh line. The collection fiber 130 then conducts only the relatively weak Raman scattering lines, as depicted in graph 134, from sample 120 to an analysis instrument such as spectrograph 140 for detection.

Compared with the non-imaged approach of the McCreery-style probes, imaged excitation and collection as just described offer smaller sample measurement areas, sharper depth-of-focus, and a variable working distance between the probe and the sample. Imaging probeheads are, however, larger, more complex and more sensitive to alignment with the sample than non-imaging fiber optic Raman probes. In addition, imaging probeheads tend to have lower throughput than non-imaging fiber optic Raman probes, throughput being defined as Raman photons delivered to the spectrograph divided by the laser power incident on the excitation optical fiber.

There is, therefore, an unfulfilled need for a fiber optic based probe that combines the strengths of the McCreery-style probe (small size, high throughput, high-temperature operation, alignment insensitivity, easily mass-produced) with the strengths of the imaging probehead (no optical fiber background, variable working distance between probehead and sample)

SUMMARY OF THE INVENTION

The present invention provides the benefits of non-imaging fiber-optic probes and those of filtered, imaging fiber-optic probes by placing the laser band-pass filter and/or the laser band-reject filters proximate to the end of the probe. In the preferred embodiment, this is done by placing an appropriate Bragg grating at the end of, and within, one or both of the optical fibers that make up the probe. Thus, where a first optical fiber is used to carry excitation energy of a nominal wavelength to a sample, an optical filter will be integral and proximate to its distal end to selectively pass energy of the nominal wavelength. Where a second optical fiber is employed to carry stimulated emission from the sample to an analytical instrument such as a spectrometer, this fiber may also have included therewithin and proximate to its distal end, an optical filter to selectively reject energy associated with the nominal wavelength. The grating in the excitation fiber is preferably chirped, whereas the grating in the second fiber may constitute a simple reflection filter. To increase collection efficiency, a plurality of second fibers may be employed, and may be grouped around one or more first fibers, each with an appropriate, integrally formed filter. In addition, arrangements including specific tip shapes and/or imaging means may be used to direct the excitation energy from the first fiber onto the sample, or to assist in directing the stimulated emission from the sample into the second fiber(s).

A representative system-level optical measurement probe according to the invention, then, would include a laser, a spectrometer, a first optical fiber to carry energy from the laser to a sample, including a Bragg grating laser bandpass filter proximate to its tip, and a second optical fiber to carry energy collected from the sample to the spectrometer, including a Bragg grating laser band-reject filter proximate to its tip. The invention may be used in any type of apparatus based upon the delivery of coherent radiation and/or collection of spectra for analysis, including Raman spectroscopy, florescence measurements, and any derivatives thereof.

DETAILED DESCRIPTION OF THE PREFERRED EMBODIMENT

This invention improves upon the filtered, non-imaging Raman probe by embedding the laser band-pass filter and/or the laser band-reject filter at or near the ends of their respective fibers. In the preferred embodiment, this is done by placing an appropriate Bragg grating within each of the optical fibers that make up the probe. The approach therefore affords the benefits of non-imaging fiber probes and those of filtered, imaging probe designs. In addition, the unique properties of Bragg gratings in optical fibers offer several capabilities beyond those of traditional, filtered fiber-optic Raman probes. For example, a probe according to the invention may be used at temperatures exceeding 500° C., operate in any spectral region from the UV through the mid-IR and perhaps, and measure Raman bands or Brillouin bands located only a few wave numbers from the laser line.

Figure 1:
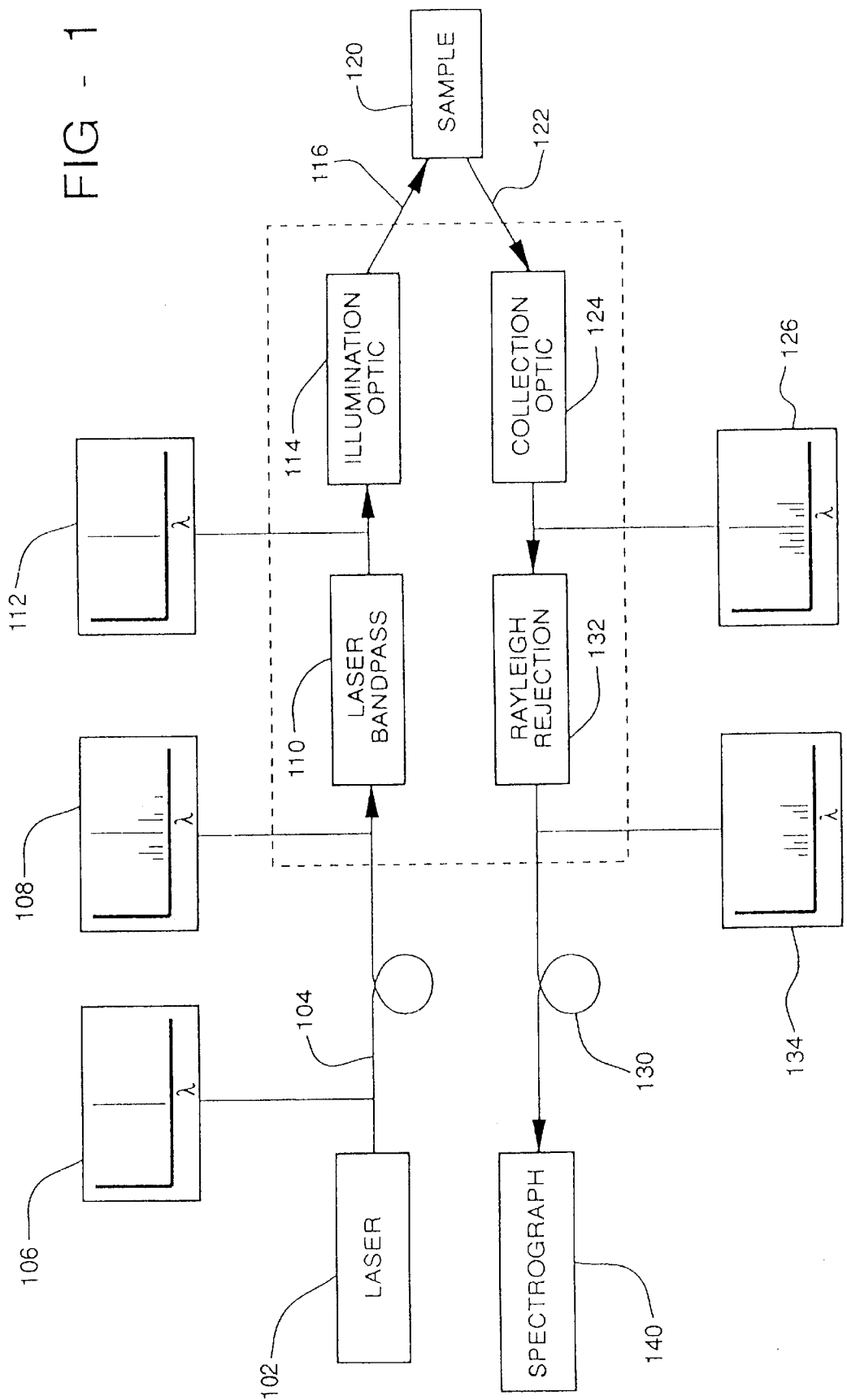
FIG. 1 is a block diagram depicting a fiber-based probe including imaging optics.
Figure 2:
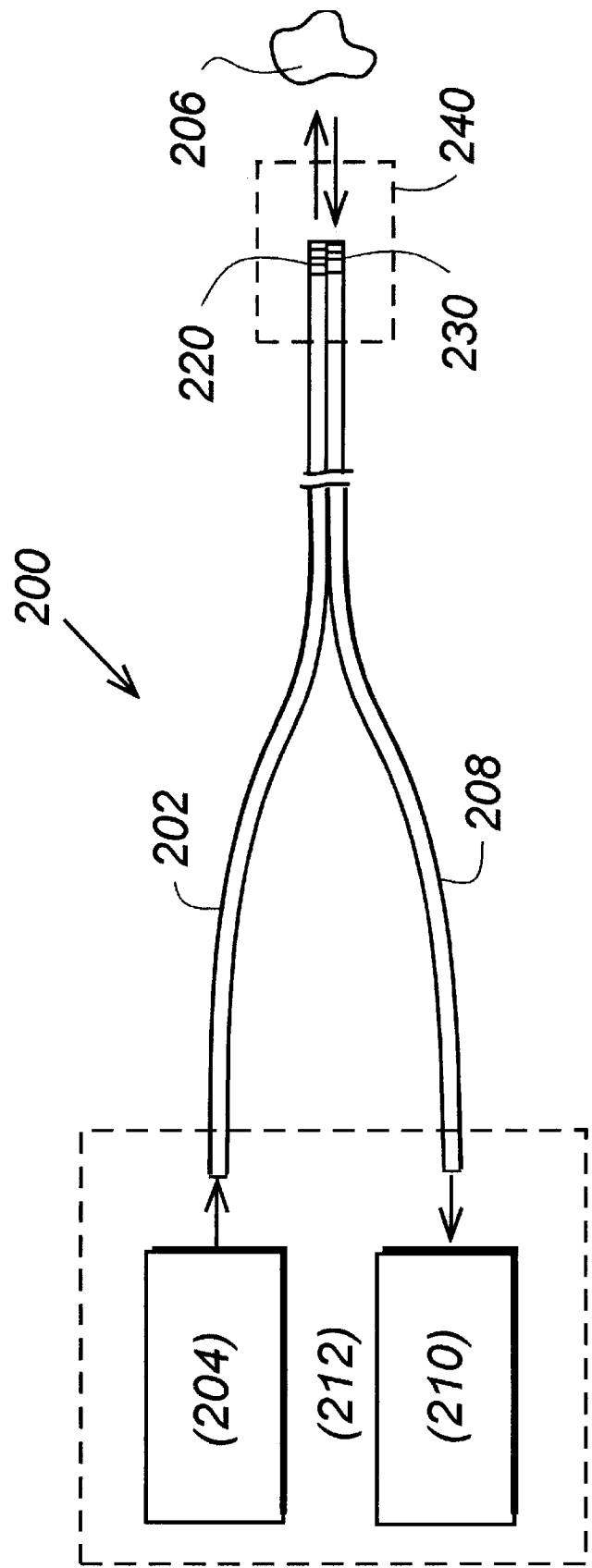
FIG. 2 is a block diagram of a system according to the invention.

In FIG. 2, a first optical fiber 202 is used to carry exitation radiation from a source 204 such as a laser to a sample 206 being characterized. Reflected or scattered radiation from the sample 206 is then carried by a second fiber 208 to a spectrometer 210 for analysis. FIG. 2 is not drawn to scale, and it should be understood that the physical configuration may depart considerably from that shown yet remain within the scope of this invention. For example, although the laser 204 and spectrometer 210 are shown to be co-resident within a box 212, one or the other device may be located more closely to the sample 206. In addition, more or fewer fibers than those shown may be employed according to the invention. Depending upon the circumstances, it is conceivable that only the exitation fiber or return fiber may be required, so that, if either is formed in accordance with the techniques described below, such a fiber would be considered as being within the scope of the appended claims. In addition, multiple fibers may be used for exitation and/or return energy; that is, approaches such as those in U.S. Pat. No. 4,573,761 may be used, wherein a single laser deliver fiber is "surrounded" by a plurality of return fibers.

Bragg gratings 220 and 230 at the probe end 240 are used to carry out the filtering operations typical of imaging type fiber-optic Raman probeheads. Specifically, the collection fiber 208 preferably uses a simple reflection filter to remove the laser line, whereas, again in the preferred embodiment, the excitation fiber 202 uses a chirped grating 220 to reflect a broad bandwidth shifted slightly to the red of the laser line.

Narrow-band, highly reflecting Bragg gratings in optical fibers were first demonstrated by Hill et al. in 1978. In 1989, Meltz et al. wrote Bragg gratings in germanosilicate optical fibers by a transverse holographic method using an interference pattern from a UV laser (see also U.S. Pat. No. 4,807,950 to Glenn et al). More recently, Hill et al. described in U.S. Pat. No. 5,367,588 a method for fabricating Bragg gratings by exposure through a phase grating mask, which simplifies the exposure process and adds flexibility to the design of the grating configuration. Treating the optical fiber with hydrogen or deuterium prior to exposure has been shown to reduce the laser energy required to write the grating. The precise mechanism for the photosensitivity of germanosilicate optical fibers is poorly understood, but it appears that at least two photorefractive effects are responsible. Bragg gratings have also been made inside optical fibers composed of other materials, such as tin-doped phosphosilicate glass or chalcogenide glass.

Glass as a holographic material requires no developing or processing, so very thick (long) gratings can easily be constructed. Bragg gratings inside single-mode optical fibers can have very narrow reflection bandwidths because the single-mode optical field can be described by a single propagation vector. As a result, the light in a single-mode optical fiber interacts with the Bragg grating in much the same way that a plane wave interacts with a stratified refractive index medium as described by Kogelnik's coupled wave theory. Fiber gratings several millimeters long have been fabricated. As expected, these gratings have reflection bandwidths of 1 cm$^{-1}$ or less.

Holograms in glass can also tolerate much higher temperatures than gelatin, which may be used in filter elements of prior-art probeheads. For example, gratings in germania-doped silica fibers can be stable at temperatures as high as 800° C. There is, of course, a wavelength shift due to thermal expansion. Precise and reproducible chirp in the fringe spacing of fiber gratings has also been demonstrated. Although chirped fiber gratings have been used for ultrafast pulse compression, their most attractive property for this invention is their broadband reflectivity and sharp cutoff edges.

EXAMPLE

In designing a Bragg grating that acts as a rejection filter for the collection fiber, if the wavelength of the exciting laser is $\lambda_0$, then the grating spacing d in the fiber to reject that wavelength is given by $$d = \frac{\lambda_0}{2*n_{eff}},$$

where $n_{eff}$ equals the effective refractive index of the fiber. For an index of 1.46 and a laser wavelength $\lambda_0$=785 nm, the grating period d is then 269 nm.

The fiber grating may be exposed with ultraviolet light at a wavelength to which the fiber is sensitive, for example, light from a KrF excimer laser at a wavelength of 249 nm. Such exposure may be carried out through a phase mask that generates an interference pattern of the ultraviolet light with a period of 269 nm. Alternatively, a two-beam holographic transverse exposure configuration could be used with an ultraviolet exposing wavelength, with the angle between the exposing beams being chosen to create an interference pattern with a period of 269 nm.

In the case of the bandpass filter at the end of the excitation fiber, a chirped grating is preferably fabricated so that the rejection bandwidth will be broad. The extent of the chirp broadens the rejection bandwidth sufficiently to reject Raman scattering generated in the excitation fiber as well as any laser emission at unwanted wavelengths. After formation of the chirped grating, the portion of the grating that reflects the excitation wavelength $_0$ can be destroyed by an additional exposure to concentrated UV light, as described by Zhang et al. In this manner, a bandpass filter is created, blocking the silica Raman and unwanted laser emission while transmitting only the laser excitation wavelength $_0$. Other grating arrangements can be used to form bandpass filters in optical fibers such as a Fabry-Perot elalon or a Michelson configuration, as described by Morey et al.

Higher-order modes in an optical fiber require a different grating spacing for Bragg reflection as compared to lower-order modes. A range of grating spacings are required to obtain high reflectivity for the set of all modes in a multi-mode optical fiber. This, in turn, broadens the reflectivity bandwidth of the device. The range of grating spacings is determined by the core-to-cladding refractive index ratio. Appropriate choice of multi-mode optical fibers may be important to reflective grating performance. Alternately, an adiabatic taper may be employed to permit narrow-band reflectivity for a large number of modes.

Several modifications to adjust the performance of the design shown in FIG. 2 are possible. In one alternative embodiment, multiple gratings may be placed in the excitation fiber 202 to reject specific wavelengths (for example, plasma lines in analytically important spectral regions). Optics to re-image the collection zone onto or into the sample may also be used to extend the working distance between the sample and the probe, since reflections from the lenses would not produce large amounts of optical fiber background at the spectrograph. High-temperature bonding materials may be used so that the probe may be directly immersed in high temperature samples. Angled or chisel-tipped non-imaging probes may also take advantage of the fiber optic grating filters according to the invention.

In summary, the invention provides a simple and economical probe for various stimulated emission applications. Once the gratings have been formed into their respective optical fibers, the resulting probe is essentially an optical device with no optical components; it is simply a pair or a bundle of optical fibers with precise filtering capabilities. As such, it is small, rugged, and readily mass-produced. The probe end may also be re-polished to a limited extent. This technology is applicable to a broad range of wavelengths and high operating temperatures. Throughput should be higher than any other filtered probe reported so far, and its sensitivity to sample placement should be much less than imaging Raman probes, making it easier to use.

I claim:

1. A fiber-optic probe adapted for use with a source of excitation energy having a nominal wavelength and means for analyzing the emission of a sample, comprising:
   a first optical fiber to carry the excitation energy to the sample, the first fiber having a distal end through which the excitation energy is delivered to the sample;
   a second optical fiber to carry the emission from the sample to the means for analyzing the emission of the sample, the second fiber having a distal end through which the emission is collected; and
   an optical filter associated with the nominal wavelength, the filter being embedded within at least one of the first and second fibers and proximate to its distal end.

2. The probe of claim 1, wherein the optical filter is embedded within the first fiber to selectively pass energy associated with the nominal wavelength.

3. The probe of claim 2, wherein the filter takes the form of a Bragg grating.

4. The probe of claim 3, wherein the grating is chirped.

5. The probe of claim 1, wherein the optical filter is embedded within the second fiber to selectively reject energy associated with the nominal wavelength.

6. The probe of claim 5, wherein the filter takes the form of a Bragg grating.

7. The probe of claim 3, wherein the grating is a reflection grating.

8. The probe of claim 5, including a plurality of second fibers, each including an embedded filter to selectively reject energy associated with the nominal wavelength.

9. The probe of claim 1, wherein the emission includes Raman scattering.

10. The probe of claim 1, wherein the emission includes fluorescence.

11. A system for obtaining the emission of a sample, comprising:
    a source of excitation energy having a nominal wavelength;
    emission analysis means;
    a first optical fiber to carry the excitation energy to the sample, the first fiber having a distal tip through which the excitation energy is delivered to the sample, the distal tip of the first fiber having embedded therein an optical filter to selectively pass energy associated with the nominal wavelength; and
    a second optical fiber to carry the emission from the sample to the emission analysis means, the second fiber having a distal tip through which the emission is collected, the distal tip of the second fiber having embedded therein an optical filter to selectively reject energy associated with the nominal wavelength.

12. The system of claim 11, wherein the emission includes Raman scattering.

13. The system of claim 11, wherein the emission includes fluorescence.

14. The system of claim 11, wherein the filters are Bragg gratings.

15. The system of claim 11, wherein the first fiber uses a chirped grating.

16. The system of claim 11, wherein the second fiber uses a reflection grating.

17. The system of claim 11, including a plurality of second fibers, each including an embedded laser band-reject filter at its distal tip.

18. The system of claim 11, wherein the second fibers are symmetrically grouped around the first fiber.

19. The system of claim 11, further including one or more optical elements for directing the excitation energy from the first fiber onto the sample.

20. The system of claim 19, wherein the arrangement includes a first fiber having a shaped distal tip.

21. The system of claim 11, further including one or more optical elements for directing the emission from the sample into the second fiber.

22. The system of claim 21, wherein the arrangement includes a second fiber having a shaped distal tip.

23. In a system wherein a first optical fiber is used to carry energy at a nominal wavelength to a sample and a second optical fiber is used to collect energy emitted by the sample, the improvement comprising:
    at least one of the fibers having an internal optical filter associated with the nominal wavelength.

24. The improvement of claim 23, wherein the first optical fiber has an internal bandpass filter.

25. The improvement of claim 23, wherein the second optical fiber has an internal band rejection filter.

* * * * *